United States Patent
Lathrop

(10) Patent No.: US 8,452,546 B1
(45) Date of Patent: May 28, 2013

(54) METHOD FOR DEDUCING A POLYMER SEQUENCE FROM A NOMINAL BASE-BY-BASE MEASUREMENT

(75) Inventor: Daniel K Lathrop, San Diego, CA (US)

(73) Assignee: Electronic Biosciences, Inc., San Diego, CA (US)

(*) Notice: Subject to any disclaimer, the term of this patent is extended or adjusted under 35 U.S.C. 154(b) by 494 days.

(21) Appl. No.: 12/614,782

(22) Filed: Nov. 9, 2009

Related U.S. Application Data

(60) Provisional application No. 61/112,351, filed on Nov. 7, 2008.

(51) Int. Cl.
  *G06F 19/00* (2011.01)
  *C12Q 1/68* (2006.01)
(52) U.S. Cl.
  USPC .............................................. 702/20; 435/6.1
(58) Field of Classification Search
  None
  See application file for complete search history.

(56) References Cited

U.S. PATENT DOCUMENTS 6,015,714 A * 1/2000 Baldarelli et al. ................. 436/2
7,731,826 B2 * 6/2010 Hibbs et al. .................... 204/450

OTHER PUBLICATIONS

Branton et al. The potential and challenges of nanopore sequencing. Nature Biotechnology vol. 26, pp. 1146-1153 (Oct. 2008).*

* cited by examiner

*Primary Examiner* — John S Brusca
(74) *Attorney, Agent, or Firm* — Diederiks & Whitelaw, PLC

(57) ABSTRACT

A method of processing sequencing data obtained with a polymer sequencing system identifies the most likely monomer sequence of a polymer, regardless of stochastic variations in recorded signals. Polymer sequencing data is recorded and two or more distinct series of pore blocking signals for a section of the polymer are recorded. A value is assigned to each series of pore blocking signals to obtain multiple trial sequences. The probability that each of the trial sequences could have resulting in all of trial sequences is calculated to determine a monomer sequence with the highest probability of resulting in all of the trial sequences, termed the first iteration sequence. The first iteration sequence is systematically altered to maximize the combined probability of the first iteration sequence leading to all the trial sequences in order to obtain a most likely sequence of monomers of the polymer.

28 Claims, 7 Drawing Sheets

$TCG_2ACTAGC_3T_2AGCA_2TCGA_3$
$TCG_{\underline{1}}ACTAGC_3T_2AGCA_2TCGA_3$ $GTACTG_3C_3ACTAGCTAGCACGT$
$GTACTG_3C_3ACTAGCTAGCACGT$ $TCG_2\ \ CT_2AC_2AT_2CTAGAGATGCAC$
$TCG_2\underline{\mathbf{A}}CT_2AC_2AT_2CTAGAGATGCAC$ $AGTAC_2T_2C_2G_2C_3TC_2GAC_2ACT$
$AGTAC_2T_2C_2G_2C_{\underline{4}}TC_{\underline{1}}GAC_{\underline{3}}ACT$ $AT_2CA_2TC_2TCA_2T_1AT_2GCAC_2TAC$
$AT_{\underline{1}}CA_2TC_2TCA_{\underline{3}}T_{\underline{2}}AT_{\underline{1}}GCAC_2TAC$ $T_2CACA_2CAGCTGC_2ATACGC_2G_3$
$T_2CACA_2CAGCTGC_2ATACGC_2G_3$ $G_4AT_2A_2CATC_2TGC_1ACTCA_2GC$
$G_{\underline{3}}AT_{\underline{1}}A_2CATC_2TGC_{\underline{2}}ACTCA_2GC$ $AGA_2T_2G_2T_2CTCGATAGCTCTAT_1A$
$AGA_2T_{\underline{1}}G_2T_{\underline{3}}CTCGATAGCTCTAT_{\underline{2}}A$ $ATAGCGATCTCG_3A_2GCA_2GT_2GT_1$
$ATAGCGATCTCG_{\underline{2}}A_2GCA_2GT_{\underline{1}}GT_{\underline{2}}$ $T_2C_2A_2G_2A_2C_2G_2TCG_2TAGCAGA$
$T_2C_2A_2G_2A_2C_2G_2TCG_2TAGCAGA$ $GACTCGAGCT_2CG_2ACGTCA_3CAT$
$GACTCGAGCT_2CG_{\underline{1}}ACGTCA_3CAT$ $ATG_3TATATC_2TC_3GT_2CTGAGT$
$ATG_3TAT\underline{\mathbf{XX}}C_2TC_3GT_2CTGAGT$ $GC_2TG_3TA_2G_2A_3GCATCTCG_2C$
$GC_2TG_3TA_{\underline{3}}G_2A_3GCATCTCG_{\underline{1}}C$ $G_2A_2TC_2A_2CAT_2CTATCGCTG_2A_2$
$G_2A_{\underline{1}}TC_2A_{\underline{3}}CAT_2CTATCGCTG_{\underline{1}}A_2$ $CTA_2C_2AC_1AGACATCTGCG_3A_2$
$CTA_4C_{\underline{1}}AC_{\underline{2}}AGACATCTGCG_3A_2$ $TGT_4GTCTG_2C_2TAGC_2TACG_2A$
$TGT_4GTCTG_2C_2TAGC_2TACG_2A$ $CGA_3TCAT_1A_2G_2A_2GTCG_2AC_2GC$
$CGA_3TCAT_{\underline{2}}A_2G_2A_2GTCG_{\underline{3}}AC_2GC$ $TC_4TACT_3AGTA_4CA_2TCAC$
$TC_4TACT_3AGTA_4CA_{\underline{1}}TCAC$ $T_3GATA_1CA_2TA_2CGCGCTAGT_2C_2$
$T_3GATA_{\underline{2}}CA_{\underline{1}}TA_2CGCGCTAGT_2C_2$

FIG. 6A $AC_2AT_1ATAGT_3AT_2GCA_2TGT_1GA_1T$
$AC\underline{1}AT\underline{2}ATAGT_3AT\underline{1}GCA_2TGT\underline{2}GA\underline{2}T$
$TGC_3T_2CA_2TGCACTGT_1GTCATG_2$
$TGC\underline{2}T_2CA_2TGCACTGT\underline{2}GTCATG_2$
$T_2GC_2GTC_3TATA_2TCATGTGCAT$
$T_2GC_2GTC\underline{2}TATA_2TCATGTGCAT$
$TA_2C_2TAGTGA_2CGTACT_2CGAGC_2$
$TA\underline{1}C\underline{1}TAGTGA_2CGTACT_2CGAGC_2$
$GT_2GACATACA_2G_2T_4ACTCT_2G$
$GT\underline{1}GACATACA_2G_2T_4ACTCT_2G$
$CTC_2GTGCGATAT_2AGT_2GCA_3TG$
$CTC\underline{1}GTGCGATAT_2AGT_2GCA_3TG$
$GTAGC_2AT_2AGT_2CGCTGACTC_4$
$GTAGC_2AT_2AGT_2CGCTGACTC_4$
$G_2TC_2GTAGTATGTACT_2CACTGA_2$
$G_2TC_2GTAGTATGTACT_2CACTGA_2$
$TACA_3TCG_2ACTG_2AGAGT_1GTG_3$
$TACA_3TCG_2ACTG_{\underline{3}}AGAGT_{\underline{2}}GTG_3$ $AGTGCAT_2AGATGCGCAC_2GC_2GAT$
$AGTGCAT_2AGATGCGCAC_{\underline{1}}GC_{\underline{3}}GAT$ $A_2TCGCG_4TAC_2A_2C_2ATCTA_2G$
$A_2TCGCG_{\underline{3}}TAC_2A_2C_2ATCTA_2G$ $AGT_2GC_3ATC_2GCT_2G_3CT_2CGC$
$AGT_2GC_3ATC_{\underline{1}}GCT_2G_{\underline{2}}CT_{\underline{1}}CGC$ $CGATATCG_2CTGAG_2C_2TA_2CT_2CA$
$CGATATCG_2CTGAG_2C_2TA_2CT_{\underline{1}}CA$ $G_3ATC_3TATA_2GCGACGACGC_3$
$G_3ATC_{\underline{2}}TA\underline{\mathbf{XX}_{2}}GCGACGACGC_3$ $AGAGTG_2CACTA_2C_2A_2TACGTCGA$
$AG\underline{\mathbf{XX}}TG_2CACTA_2C_2A_2TACGTCGA$ $GTACG_3TCG_2C_3G_3C_2TC_3TA$
$GTACG_3TCG_2C_{\underline{2}}G_3C_2TC_{\underline{2}}TA$ $TAGAGACG_2CTAGA_2GTATG_2AG_2A$
$TAG\underline{\mathbf{XX}}ACG_2CTAGA_2GTATG_{\underline{1}}AG_2A$ $A_2CAGATAG_2CT_2CAGA_2TAGTG_2A$
$A_2CAGATAG_2CT_2CAGA_{\underline{1}}TAGTG_2A$ $CTCT_2A_2TGACGAC_2T_3A_2GCTGC$
$CT\underline{\mathbf{XX}_{2}}A_2TGACGAC_2T_{\underline{2}}A_2GCTGC$

FIG. 6B $G_2AGC_2GTACGAGAGC_3T_2A_2GCG$
$G_2AGC_2GTACGAGAGC_3T_2A_2GCG$
$C_2ATAG_2C_2TAGATC_2GT_1GT_2C_2G$
$C_2ATAG_2C_2TAGATC_2GT_2GT_1C_2G$
$ATC_2GCGAGA_2TC_2GCAGATGT_3A$
$ATC_2GCGAGA_2TC_2GCAGATGT_3A$
$ATCATATGCTGCTGCT_4C_3G_2A$
$ATCATATGCTGCTGCT_4C_3G_2A$
$C_3TAGTCATC_3ACT_2CGT_1GTA_3$
$C_3TAGTCATC_3ACT_3CGT_2GTA_3$
$GC_2GAGATAT_2GA_2TGCTA_2TACTG$
$GC_1GAGATAT_2GA_2TGCTA_2TACTG$
$GT_2CTCGTGATG_3CT_2GCACTACA$
$GT_1CTCGTGATG_2CT_2GCACTACA$
$GC_2ATGCA_2C_2TGT_3CG_3T_2G_2C$
$GC_1ATGCA_2C_2TGT_3CG_3T_2G_1C$
$ACTA_2GCACG_2CGC\ GCGACA_2GAG$
$ACTA_1GCACG_2CGC\underline{T}GCGACA_2GAG$
$GC_2A_3C_2ATCAC_1ATGC_2GC_3TG_2$
$GC_1A_2C_3ATCAC_2ATGC_2GC_2TG_2$
$TC_2GCAGCGCTCAG_3ACGA_2CT_2G$
$TC_2GCAGCGCTCAG_3ACGA_2CT_2G$
$GTACA_1C_2ATGCTC_3TGATGC_3GT$
$GTACA_2C_2ATGCTC_3TGATGC_2GT$
$ACA_3GCGACTA_3TGC_2TC_2T_2CA$
$ACA_3GCGACTA_3TGC_2TC_2T_2CA$
$GAGC_2GCGTG_1TATA_3GAT_2C_3AG$
$GAGC_2GCGTG_2TA\underline{XX}_3GAT_2C_3AG$
$CA_2C_2GTAGTGTAC_2GA_4T_2CA_2$
$CA_1C_2GTAGTGTAC_2GA_4T_2CA_2$
$GTAGTA_2T_1ATATGTCT_3C_2G_2TCT$
$GTAGTA_2T_1AT\underline{XX}GTCT_3C_2G_2TCT$
$CAT_2ACT_2ACG_2TACG_2ATCACTG_2$
$CAT_1ACT_2ACG_1TACG_2ATCACTG_3$
$TCGTGTGC_2T_2ACGTAG_3AGT_2GT$
$TCGTG\underline{XX}C_2T_2ACGTAG_3AGT_2GT$
$CATG_2AGTCGCGT_2AC_2TAGACTGA$
$CATG_1AGTCGCGT_2AC_2TAGACTGA$

FIG. 6C

METHOD FOR DEDUCING A POLYMER SEQUENCE FROM A NOMINAL BASE-BY-BASE MEASUREMENT

CROSS-REFERENCE TO RELATED APPLICATIONS

The present invention claims the benefit of U.S. Provisional Patent Application Ser. No. 61/112,351 entitled "Data Processing Method for Deducing a Polymer Sequence from a Nominal Base-by-Base Measurement" filed Nov. 7, 2008.

STATEMENT REGARDING FEDERALLY SPONSORED RESEARCH OR DEVELOPMENT

This invention was made with government support under Contract No. W911NF-08-C-0046 awarded by the Army Research Office and the Defense Advanced Research Projects Agency and Contract No. 2R44HG004466-02 awarded by the National Institute of Health, specifically, the National Human Genome Research Institute. The government has certain rights in the invention.

BACKGROUND OF THE INVENTION

Extensive amounts of research and money are being invested to develop a method to sequence DNA, (Human Genome Project) by recording the signal of each base as the polymer is passed in a base-by-base manner through a recording system. Such a system could offer a rapid and low cost alternative to present methods based on chemical reactions with probing analytes and as a result might usher a revolution in medicine.

Research in this area to date has focused on the question of developing a measurement system that can record a sufficient signal from each monomer in order to distinguish one monomer from another. In the case of DNA, the monomers are the well-known bases: adenine (A), cytosine (C), guanine (G), and thymine (T). It is necessary that the signals produced by each base be: a) different from that of the other bases, and b) different by an amount that is substantially larger than the internal noise of the measurement system. This aspect of sequencing is fundamentally limited by the specific property of the polymer being probed in order to differentiate the monomers and the signal to noise ratio (SNR) of the measurement device used to probe it.

A separate question is the order in which the monomers are measured. In order to know which monomer (or group of monomers) is being measured, it is necessary to localize the polymer to a precision comparable in length to the monomer itself. Controlling the polymer position and motion at such short length scales is challenging, in particular the polymer is subject to diffusive (Brownian) motion due to the impact of other molecules in solution.

One popular method to limit the polymer motion is to pass it through a nanopore, an approximately cylindrical cavity in a solid substrate with diameter equal to or a little larger than the polymer of interest. For such a nanopore, the polymer motion is effectively in one dimension (1-D) along the axis of the pore, but is still subject to stochastic variations in this 1-D motion due to Brownian effects. Specifically, Brownian motion results in a "random walk" such that the mean square displacement in a given time t is given by 2Dt for a polymer of diffusion constant D. This random motion is added to the imposed translocation motion, resulting in an inherent uncertainty in the number of bases that have passed through the measurement device. For example, for DNA confined within an alpha-hemolysin (aHL) protein pore at 15° C., the mean net 1-D motion due to diffusion alone in 100 microseconds ($\mu s$) is approximately 5 bases. Thus, in a notional example in which a given base is measured for 100 $\mu s$, the DNA would on average have moved a linear distance away from its desired position a total of 5 bases in either direction due to diffusion, resulting in, in this example, a segment of the DNA being re-measured or skipped. Such positional errors can occur no matter how sensitive the measurement system is that identifies each base.

Recent discoveries have shown that physical changes such as cooling the electrolyte and changing the viscosity of the electrolyte can reduce the diffusion constant of DNA in $\alpha$HL by a considerable factor. However, even with such measures, methods proposed to sequence DNA by recording the signal of each base in a serial manner are still expected to have sequence order errors exceeding the current benchmark target of 99.99% accuracy. Accordingly, what is needed in order to develop a practical polymer sequencing system from such new approaches is a method to process data in order to reduce the effect of stochastic variations in the polymer position.

SUMMARY OF THE INVENTION

The method of the present invention utilizes a combination of data processing steps to limit the sequencing error produced by stochastic motion of a polymer in solution, and thereby improves the sequencing accuracy of the overall sequencing system. Initially, a polymer sequencing system, such as a nanopore sensing system, is utilized to record sequence data. The input data for the method of the present invention is an observation of the time series recording of the signal produced as a polymer passes through the nanopore of the sensing system. Two or more observations of each section of the polymer to be sequenced are made. The observations can be made by repeatedly measuring the same polymer molecule, by measuring multiple molecules of the same polymer, or by a combination of both methods. The first step in the data processing method of the present invention is to assign a value to each apparent monomer in each of the observations based upon foreknowledge of the signal amplitude produced by each monomer, and a physical model of the underlying process by which the polymer moves through the device. The outcome is a set of M (M$\geq$2) trial sequences, one trial sequence for each observation.

The second step is to assume in turn that each particular trial sequence is true and calculate the total probability that this particular sequence could have resulted in all of the M observations. The total probability is calculated from the known statistics of the underlying stochastic processes that lead to the variations in polymer position. The trial sequence with the highest total probability of resulting in the complete set of observations is chosen as the first iteration.

In the preferred embodiment, a third step comprises systematically altering the first iteration sequence to maximize the combined probability of its leading to the M observations. In the simplest embodiment, it is assumed that all changes are local, involving only one or two adjacent monomers, and at each position a small set of likely changes is evaluated to see if any improves the combined probability, with the probabilities calculated as for the second step. If the combined probability improves, the change is kept and the process continues. This is done consecutively for each monomer position in the first iteration sequence, and then started again from the beginning and repeated until an entire sweep through the positions results in no further statistically relevant improvement.

The invention is not specific to the method used to identify an individual monomer and can in principle be utilized in combination with any method that seeks to sequence a polymer, or indeed any method that measures a property of polymer that is subject to stochastic variations in the order in which the monomers are measured, and in the duration of the event associated with each monomer. The invention also does not require that the polymer remain intact during the measurement process and applies to cases in which the observations are made on multiple individual molecules that are nominally the same.

BRIEF DESCRIPTION OF THE DRAWINGS

FIGS. 6A-6C include illustrative sequencing information generated utilizing the method of the present invention identified as SEQ ID NOS: 1-114.

DETAILED DESCRIPTION OF THE PREFERRED EMBODIMENT

Figure 1:
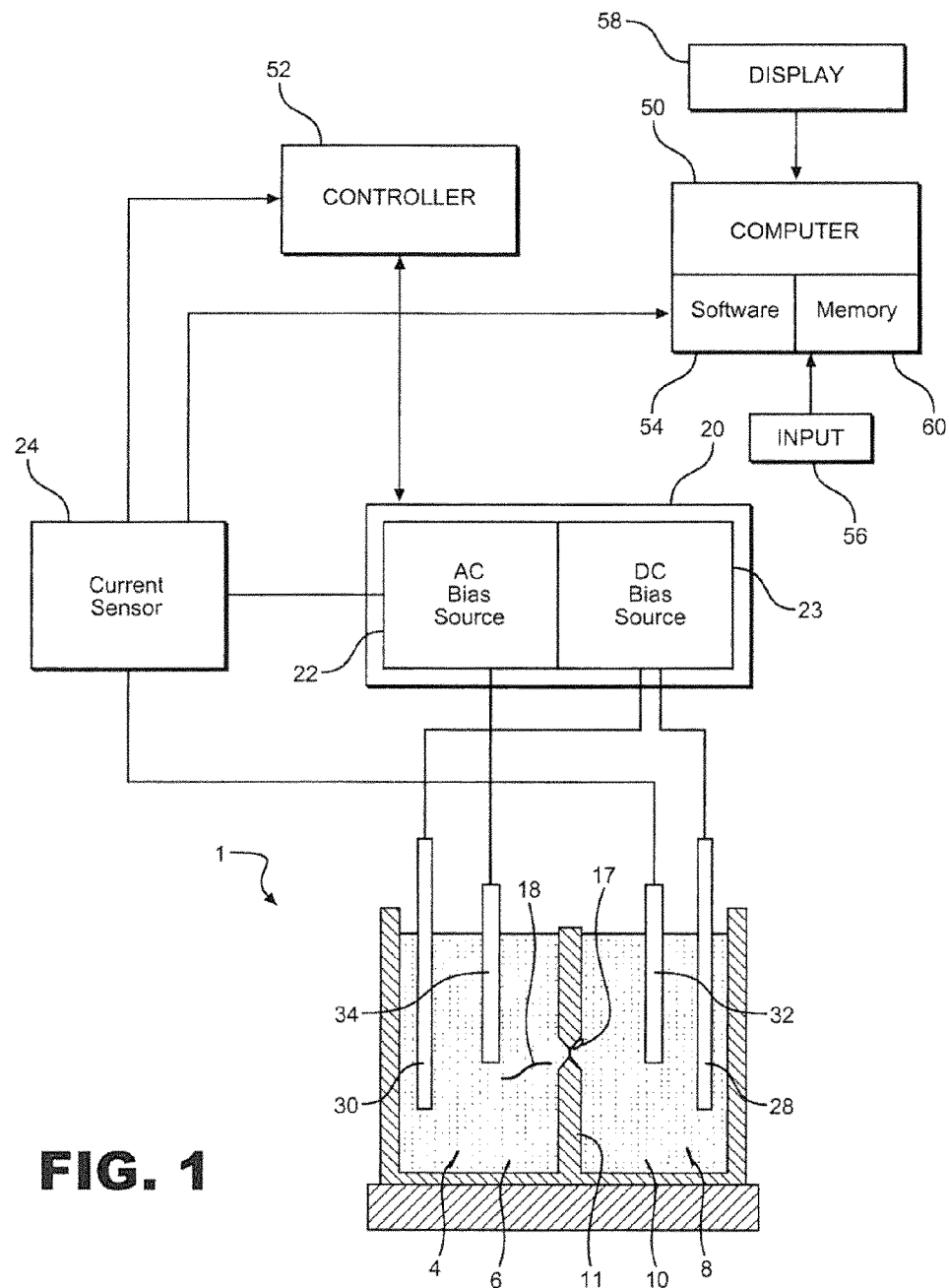
FIG. 1 depicts a polymer sequencing system for use with the method of the present invention.

With initial reference to FIG. 1, a polymer sequencing system or sensing system 1 is utilized in accordance with the present invention. In general, sensing system 1 includes a first fluid chamber or electrolyte bath 4 within which is provided a first solution or electrolyte 6, and a second fluid chamber or sensing volume 8 provided with a second electrolyte 10. Sensing volume 8 is separated from electrolyte bath 4 by a barrier structure 11, which includes a nanopore or nano-scale orifice 17 that provides a fluid path connecting the first and second electrolytes 6 and 10. In one preferred embodiment discussed herein, orifice 17 is in the form of a protein pore embedded in a lipid bilayer across an opening in barrier structure 11 in a manner known in the art. In general, sensing system 1 controls the translocation of a polymer indicated at 18 through orifice 17 utilizing a translocation means or means for controlling the velocity of a polymer through orifice 17 in the form of a power source 20. In the embodiment shown, translocation power source 20 includes an AC bias source 22 and a DC bias source 23. In addition, a current sensor 24 is provided to measure the AC current through orifice 17 produced by the AC bias source 22. More specifically, current sensor 24 is adapted to differentiate monomers of a polymer on the basis of changes in the electrical current that flows through orifice 17. In a manner known in the art, electrodes 28, 30, 32 and 34 are utilized in conjunction with current sensor 24 and power source 20. A controller 52 may be utilized to control system 1. Current signals detected or measured by current sensor 24 are processed in order to calculate a nominal monomer sequence of polymer 1. For purposes of the present invention, the term "observation" is used to describe measurements of a region of a polymer taken over time utilizing a sensing system, such as sensing system 1. The method of the present invention utilizes two or more repeat observations of the same region of one or more polymers. In general, sensing system 1 is provided for illustrations purposes only, and it should be understood that any equivalent means for detecting individual monomers of a polymer may be utilized in conjunction with the present method.

In accordance with the method of the present invention, sensing system 1 is in communication with means for deducing the sequence of a polymer from the nominal monomer sequences sensed by current sensor 24, such as computer 50. In a preferred embodiment, computer 50 includes software 54 configured to perform the method for deducing the sequence of a polymer of the present invention. Preferably, observations which are determined to have inadequate data quality (e.g., poor measurements) are excluded from the recorded observations processed by the method of the present invention. Computer 50 additionally includes an input device indicated at 56 for entering data, a display 58 for viewing information and a memory 60 for storing information.

The invention applies to polymers in general and to any method that seeks to sequence a polymer by measuring its monomers in a serial manner, but because of its technological significance and large body of existing experimental data, specific examples herein are discussed in terms of sequencing DNA. Further, because of its relative maturity and simplicity among serial-read methods, simulated data for the protein pore current blockade (PPCB) approach of sequencing DNA is utilized in order to illustrate the steps of the invention. However, it should be understood that the method of the present invention is not limited for use with DNA, nor the PPCB measurement method.

Figure 2A:
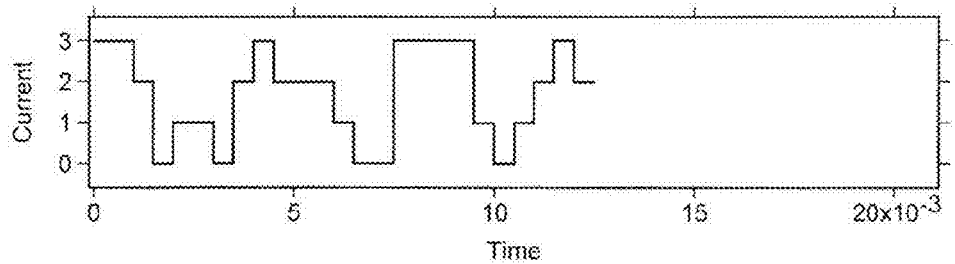
FIG. 2A is a graph depicting a model recording of pore current blockage signals over time for a 25-base ssDNA random sequence.
Figure 2B:
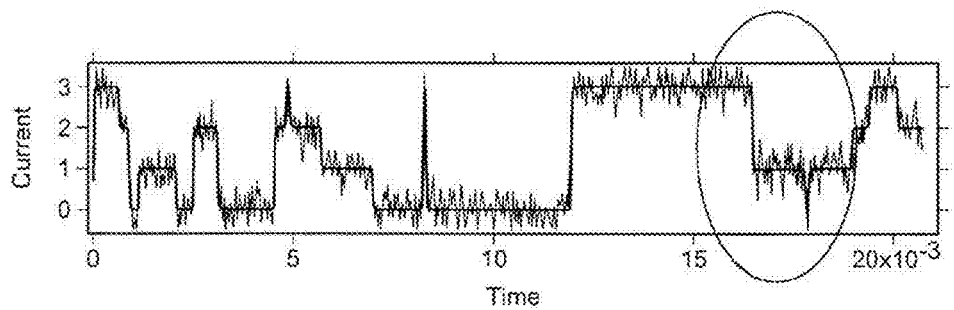
FIG. 2B is a graph depicting a first simulated recording of pore current blockage signals over time for the 25-base ssDNA of FIG. 2A.
Figure 2C:
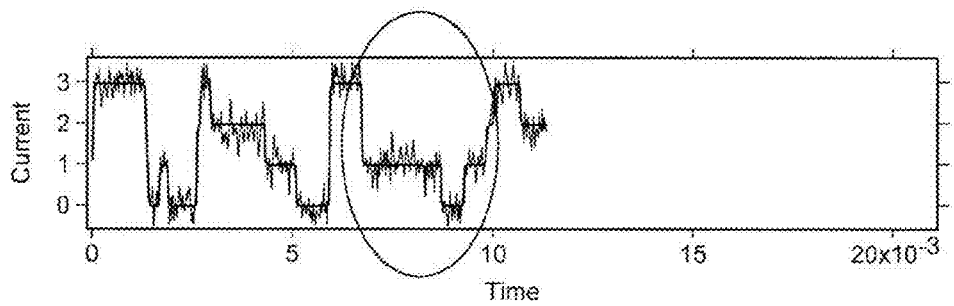
FIG. 2C is a graph depicting a second simulated recording of pore current blockage signals over time for the 25-base ssDNA of FIG. 2A.
Figure 2D:
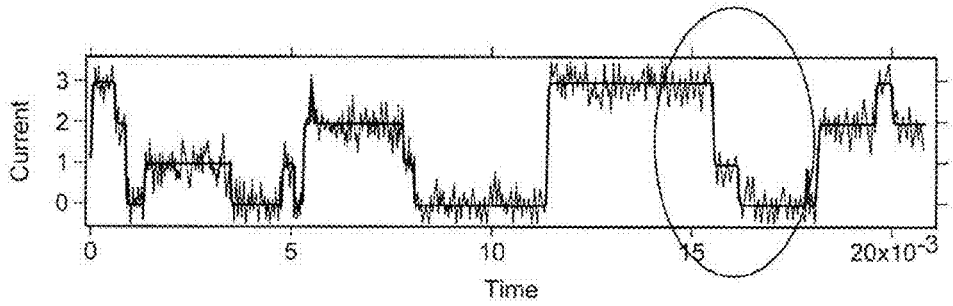
FIG. 2D is a graph depicting a third simulated recording of pore current blockage signals over time for the 25-base ssDNA of FIG. 2A.

In the PPCB approach, a signal indicative of each base is obtained via the reduction in the ionic current passing through pore 17 when a base of polymer or DNA 18 is present in pore 17. FIGS. 2A-2D illustrate the differences that may occur during separate sequencing sessions of the same DNA strand. More specifically, FIG. 2A illustrates a model recording of pore current blockage signals over time, without the effects of noise and diffusion, for a 25-base ssDNA random sequence of CCAGTTGACAAATGGCCCCTGTACA (SEQ ID NO: 115), wherein for the purposes of illustration, C is assigned a current blocking value of 3, A has a value of 2, G has a value of 0 and T has a value of 1. FIGS. 2B-2D depict three simulated PPCB signal recordings (or observation recordings) as a function of time for the translocating DNA sequence of FIG. 2A, calculated for system parameters of −10° C., 10 kHz bandwidth, 0.33 pArms system noise and a 110 mV DC bias. A fit to each observation recording is shown by the solid line. An example of equivalent regions in FIGS. 2B-2D is given by the ellipses.

It is evident that, while very similar, the mathematically generated records in FIGS. 2B-2D contain differences in duration, despite being for the same input sequence of DNA. These differences arise because of the inherent uncertainties in the stochastic motion of the DNA through the pore. An immediate example is the factor of 2 variations in total translocation time for the three simulated datasets shown in FIGS. 2B-2D. Looking more closely at the graph in FIG. 2C (reading from left to right), we see that the first transition from a 3 pA to 2 pA blockade current is missing as compared to FIGS. 2B and 2D. A second example is the variation in duration of the first 1 pA level in FIGS. 2B-2D. More specifically, in FIG.

2D the duration at this level is approximately 13 times longer than in FIG. 2C, while in FIG. 2B it is approximately equal to the idealized dwell time in FIG. 2A.

Figure 3:
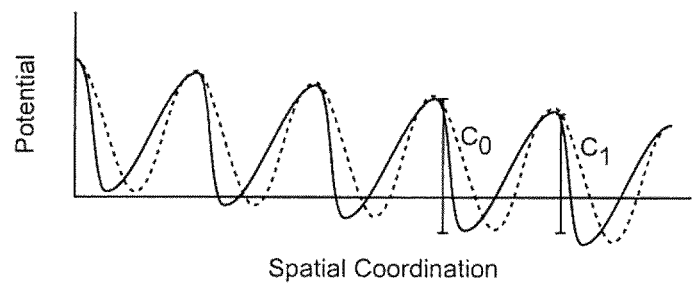
FIG. 3 is a graph of potential vs spatial coordination of a particle being sequenced.

Although individual diffusion events are stochastic, the overall statistical distribution in the case of a diffusion process is well defined. For example, one dimensional diffusion along the axis of a nanopore can be described mathematically as the motion of a rigid particle in a periodic potential. The application of a voltage to pull the DNA through the nanopore corresponds to a tilt in the potential, as shown in FIG. 3. In the limit of large barrier height, the motion can be described as thermally activated hopping from one potential minimum to the next.

The height of the potential barrier (C0, C1) can be determined from the variation of the measured diffusion constant with temperature. For example, for single strand DNA (ss-DNA) in the protein pore alpha hemolysin ($\alpha$HL) the activation energy, E, for a simple series of adenosine (A bases) (at zero potential tilt)=$1.8 \times 10$-19 Joules=108 kJ/mole. At room temperature (20° C.), the value of $1.8 \times 10$-19 Joules is 45 times kbT (where T is the temperature of the solution in Kelvins and kb is a constant, known as Boltzmann's constant), which shows that under all likely experimental conditions, ssDNA motion in $\alpha$HL can be accurately described as thermally activated hopping between minima of the 1-D potential.

A particular impact of being in the thermal activated hopping regime is that the target molecule (e.g., DNA) to be sequenced hops at a time determined by the statistics of thermal activation. Thus, equivalent to the uncertainty in the direction and total number of hops in the position of the target polymer is uncertainty in the time when it moves. This means that whatever time interval is chosen between individual measurements, it is not possible to be certain the molecule has hopped to the next minimum (as desired), hopped to the previous minimum, stayed at the same minimum, or hopped two or more times, skipping one or more bases. To minimize the impact of a hop occurring before a measurement is completed, the measurement time should be minimized. However, it is generally the case that the shorter the measurement time the less accurate the measurement, so there is a practical limit to the data acquisition rate.

Activation over a potential barrier is a paradigm statistical process, the dynamics of which apply to chemical reactions such as enzymes that process DNA. Thus, while new approaches which utilize chemical synthesis or base cutting processes to control the order the bases are measured may seem quite different, in reality, the arrival and dwell time of the bases at the detection zone in these schemes are also subject to random fluctuations in a similar manner as discussed for PPCB-based sequencing. For example, consider the case where the DNA is cut into individual deoxy nucleotide monophosphates (dNMP) at the opening to the pore in a manner that allows the dNMPs to sequentially enter and block the pore. Some dNMPs will escape without blocking the pore and thus be skipped, some dNMP blocking events may happen too close together for both to be resolved (i.e., also skipped), and some may remain bound so long that they are counted as a repeat instance of the same base. In addition, it is not required that the stochastic nature of the disturbance of the base order be specifically thermally activated, and any process that introduces a variation can be addressed by the invention, provided that its statistical distribution can be characterized.

The starting point for the invention is that when the dynamics of the polymer motion are subject to stochastic processes, averaging multiple observations of the same polymer region will lead to meaningless intermediate data values that will only increase the error in identifying the monomers. Accordingly, the present invention utilizes an algorithm to quantize the data into an estimate of the monomer sequence as a first step, and only thereafter incorporates information from additional observations of the same sequence segment.

Figure 4:
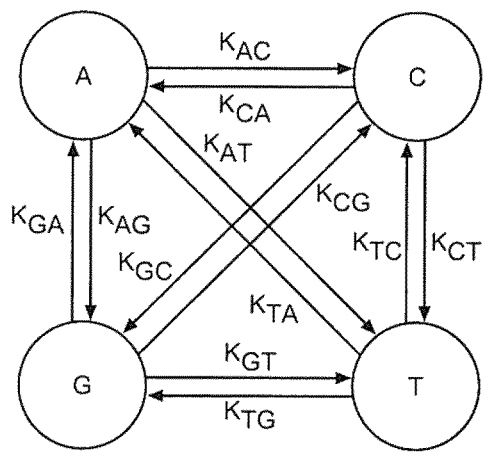
FIG. 4 is a base identification model for use with the present invention.

In the DNA example, if the measurement process has the amplitude of the signal caused by the identity of the single monomer at a sensitive site, one way to quantize the initial data into specific monomers is to apply a simple four state hidden Markov Model (HMM) with one state for each base type (shown in FIG. 4). An HMM is a well known statistical model in which the system being modeled is assumed to be a Markov process with unobserved state. By applying the forward-Viterbi algorithm to each observation, the most likely series of bases can be extracted, along with the time duration the system spends at each base between state changes. The forward algorithm is known to those skilled in the art as an algorithm for computing the probability of a series of observed events. The output of this single base model is thus a sequence in which each base is different.

If the measurement process is such that multiple bases are measured at the same time and contribute to the recorded signal, then this first level model (HMM1) must have more states. For instance, if the sensitive region of the measurement encompasses two base positions, the model must have a state for each possible two base sequence, for a total of sixteen states ($4^n$ states where 4 is the number of base types and n is the estimated number of bases contributing to the measured signal). In this case, the signal produced is likely to have degeneracies (i.e., the base pair AT might produce the same signal as the base pair CG). These degeneracies may be resolved by considering the prior and following signals. For example, if the prior signal indicates the state GA and the following indicates TG, then the state AT is chosen over CG. The output of this two base model will also be a sequence in which each base is different. Conceptually, if the signal is produced by more than two bases, an n base model can be used with a state for each possible n base sequence.

A first estimate of the number of repeat instances of each base can be obtained from the duration the system spends in each state. Alternatively, the number of repeats can be estimated for each monomer at the end of Step 2 (discussed below) from the distribution of observation times for that monomer.

The first step of the algorithm of the present invention is equivalent to algorithms that are commonly utilized for extracting idealized ion channel currents from background noise. However, to improve upon these algorithms we note that, independent of the accuracy in distinguishing bases from one another, there will be errors in the order the bases arrive at the measurement system due to the influence of stochastic processes. Specifically, sensing systems, such as sensing system 1, will occasionally jump to the next base (or further) within the measurement window allocated per base, or step back to a previous base.

To reduce the impact of the above statistical fluctuations, sequencing measurements in accordance with the present invention are performed a total of M times (M$\geq$2) to produce a set of M observations, each observation consisting of a series of measurements. In one embodiment of the invention, the set of M observations can be obtained by measuring different polymers or regions of different polymers containing the same monomer sequence. In other words, multiple observations of the same region of one or more polymers are recorded using sensing system 1. In another embodiment of the invention, the set of M observations can be obtained by measuring the same polymer or region of a polymer multiple times. One method of measuring the same polymer or region of the polymer involves reversing the direction of motion of the polymer through orifice 17 during sequencing. This reversal can be performed repeatedly to record multiple observations of the polymer during both the forward and backward motion of the polymer.

Figure 5:
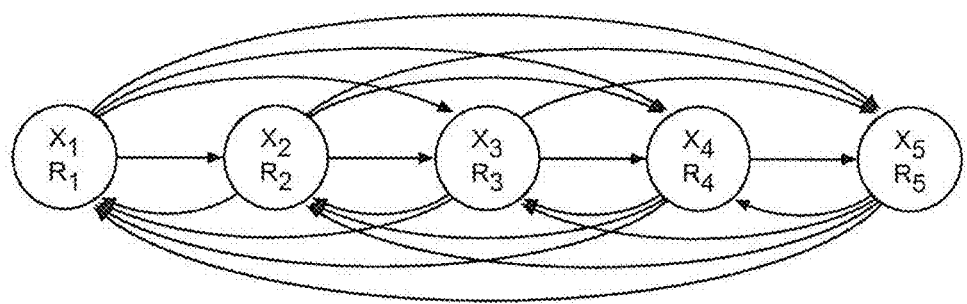
FIG. 5 depicts a Sequence Hidden Markov Model.

For each of the M observations recorded, a first level Hidden Markov Model (HMM1) is utilized to produce a likely sequence of bases or likely monomer sequence. We term each of these M sets of provisional serial base values a trial sequence. If an observation is of poor quality, as judged by the confidence level of the HMM1, or the signal to noise ratio of the measured data, or another metric, the observation can be discarded and additional data collected. We term the chosen set of M trial sequences a complete set of observations. In Step 2 of the method, we then use each of the M trial sequences to construct a Hidden Markov Model representing that sequence. This Sequence Hidden Markov Model (SHMM) is comprised of a base sequence $X_i$, including for each base in the sequence a repeat number $R_i$, as illustrated in FIG. 5. The parameters needed to use the standard HMM algorithms are the transition probabilities $T_{ij}$ defining the probabilities of a transition from state $X_i$ to state $X_j$, the start probabilities $S_i$ defining the probabilities that the first measurement is of state $X_i$, and the observation probabilities $O_{ki}$ defining the probability that we observe the current $I_k$ for duration $D_k$ given that we are in the state $X_i$ with base repeat $R_i$. Also included is a finishing probability that the system exits from the state $X_i$. The SHMM model differs from a strict HMM in that the transition probabilities and the observation probability depend not only on the present state, but also on the direction of the previous hop.

In our example of ssDNA being sequenced by the PPCB method, the probabilities are calculated from the well defined statistical processes of the activated hopping regime and measurements of the diffusion of known polymers. The measurements may indicate that the transition probabilities are dependent on the identity of the monomer being measured, the applied voltage, and on the direction of the motion of the polymer.

For example, the transition probability from state $X_i$ to state $X_j$ consists of two parts. First is the probability of a jump forward or backward, depending only on if i>j or i<j. If |i−j|=1, this is the complete transition probability from state $X_i$ to $X_j$. For |i−j|>1, we must also include the probability that intervening states are skipped over in less than one measurement time. Similarly, the probability of a jump forward or backward depends not only on whether i>j or i<j, but also on the number of base repeats $R_i$ in state $X_i$, and, if $R_i$>1, on whether the last step was forward or backward. For example, for $R_i$=2 we define $P_2$ as the probability of a forward jump given that the system still needs to make two forward jumps to get to the state $X_{i+1}$, and define $P_1$ as the probability of a forward jump given that the system needs to make only one more forward jump to get to the state $X_{i+1}$. From such considerations, we can then derive equations for the probability of a forward jump when the prior jump was forward or backward, respectively, and similar equations for the probability of a backward jump. This can be generalized to higher values of $R_i$, defining $P_k$ as the probability of a forward jump when k forward jumps are needed to reach $X_{i+1}$, leading to a matrix of transition probabilities.

Each of the M SHMMs, each representing one of the M trial sequences, are run through a modified Viterbi algorithm against all of the M observations. This modified Viterbi algorithm is modified from the standard Viterbi algorithm to account for the dependence of the transition and observation probabilities on the direction of the previous step. The output of this modified Viterbi algorithm is the combined probability that the given SHMM produced all of the M observations. By quantifying the probabilities, we can identify the trial sequence, represented by its SHMM, with the highest combined probability as the first iteration $F_1$ in the search for the optimal sequence.

The third step is to systematically alter the $F_1$ sequence to maximize the combined probability of its leading to the M observations. In the simplest embodiment, we postulate that all changes are local, involving only one or two adjacent bases, and at each position we evaluate a small set of likely changes to see if any improves the combined probability. If the combined probability improves, we keep the change and move on. This is done for each position in order, until an entire sweep through the positions results in no further statistically significant improvement. Sequence variations are chosen from a set of statistically most likely changes. The changes used in the first embodiment along with examples of them, are summarized in Table 1 below.

TABLE 1

Local sequence changes to the $F_1$ used to generate an optimum sequence.

| Change | Description | Permutations | Example |
|---|---|---|---|
| Base insertion | Insert a nonmatching base before the current base | 2 | AG → ACG or ATG |
| Double insertion | Duplicate current base and following base | 1 | AGCT → AGCGCT |
| Base change | Change the current base to a nonmatching base | 1 or 2 | AGC → ATC<br>AGA → ACA or ATA |
| Base deletion | Delete the current base (Avoiding repeat bases) | 1 or 0 | AGC → AC<br>AGA → AA not allowed |
| Double deletion | Delete the current base and the following base (Avoiding repeat bases) | 1 or 0 | AGCT → AT<br>AGCA → AA not allowed |
| Change base repeat | Change the current base repeat count | Undetermined | A3 → A4 |

As an example, the specific embodiment of the invention described above was run on computer generated data sets of the type shown in FIG. 2. A total of 57 random 25-base sequences were input into the model and 25 possible time records were generated for each of the 57 random input sequence. FIGS. 6A-6C illustrate the 57 trial sequence pairs identified as SEQ ID NOS: 1-114, where the top sequence of each pair shown in FIGS. 6A-6C is the randomly generated "true" sequence, and the lower sequence of each pair shown in FIGS. 6A-6C is the optimum sequence generated by the invention. Characters underlined and in bold indicate the location and nature of an error in the calculated optimum fit.

Although described with reference to a preferred embodiment of the invention, it should be understood that various changes and/or modifications can be made to the invention without departing from the spirit thereof. For example, although an AC current blocking sensor is utilized in the example of a possible means for detecting polymer pore blocking signals, it should be understood that a DC current sensing system or other known monomer detecting system can be utilized with the present invention. In general, the invention is only intended to be limited by the scope of the following claims.

What is claimed is:

1. A method for deducing a most likely sequence of monomers of a region of a polymer from measurements that are made nominally in sequential order, but for which an arrival time and/or an order of the monomers is subject to stochastic variations, the method comprising:
   driving one or more polymers into a nanopore;
   recording two or more observations of the same region of the one or more polymers, wherein the observations are a series of measurements of predetermined duration;
   allocating a discrete monomer identity to each apparent monomer occurrence in the two or more observations to produce a trial sequence of monomers, which could produce a complete set of observations, for each of the two or more observations;
   quantifying a probability that each trial sequence of monomers could produce the complete set of observations, based on known statistics of a sensing process utilized in recording the two or more observations of the same region of the one or more polymers; and
   selecting the trial sequence of monomers with the highest total probability as the most likely sequence of monomers of the region of the one or more polymers.

2. The method of claim 1, further comprising:
   systematically conducting sequence variations at each monomer of the most likely sequence of monomers to increase a combined probability of the complete set observations.

3. The method of claim 2, wherein the sequence variations are local and involve only one or two adjacent monomers.

4. The method of claim 2, wherein the sequence variations are chosen from a set of statistically most likely changes.

5. The method of claim 2, further comprising:
   repeating the step of systematically conducting sequence variations at each monomer until the step results in no further statistically significant increase in the combined probability of the complete set of observations.

6. The method of claim 1, wherein each measurement in an observation is allocated to the combined identity of two or more monomers in the one or more polymers.

7. The method of claim 1, further comprising:
   removing one or more of the observations that are determined to have inadequate data quality prior to allocating a discrete monomer identity to each apparent monomer occurrence in the two or more observations.

8. The method of claim 7, further comprising:
   recording additional observations of the same region of the one or more polymers based on how many observations were removed.

9. The method of claim 1, wherein the same region of the one or more polymers constitutes the entire polymer.

10. The method of claim 1, wherein two or more of the observations are of the same region of an individual polymer molecule.

11. The method of claim 1, further comprising:
    driving the one or more polymers through a nanopore in a first direction at least once to obtain a one of the two or more observations; and
    driving the one or more polymers through the nanopore in a second direction at least once to obtain another one of the two or more observations.

12. The method of claim 11, wherein allocating a discrete monomer identity to each apparent monomer occurrence is performed based on a set of sensing system parameters, and the set of sensing system parameters used to allocate the discrete monomer identities for the observations obtained by driving the one or more polymers through the nanopore in the first direction are different from the set of sensing system parameters used to allocate the discrete monomer identities for the observations obtained by driving the one or more polymers through the nanopore in the second direction.

13. A method of processing observations obtained with a polymer sequencing system adapted to detect pore blocking signals of a polymer, the method comprising the steps of:
    (a) driving a polymer into a nanopore;
    (b) assigning a value to each pore blocking signal in an observation to obtain a trial sequence, wherein the observation constitutes a series of distinct pore blocking signals recorded during sequencing of a portion of the polymer;
    (c) repeating step (b) to obtain at least a total of M trial sequences from M observations, wherein M≧2; and (d) calculating probabilities that each of the M trial sequences could have resulted in all of the M observations to determine a monomer sequence with the highest probability of resulting in all of the M observations, the trial sequence with the highest probability being a first iteration sequence.

14. The method of claim 13, wherein the value is based on a known pore blocking signal associated with a monomer and a process by which the polymer moves through the polymer sequencing system.

15. The method of claim 13, further comprising the step of: recording multiple observations.

16. The method of claim 15, further comprising the step of:
driving the polymer in a first direction through a nanopore in the sequencing system to obtain a first of the multiple observations; and
driving the polymer in a second direction through the nanopore in the sequencing system to obtain a second of the multiple observations.

17. The method of claim 16, wherein assigning the value to each pore blocking signal is performed based on a set of parameters of the polymer sequencing system, and the set of parameters used to assign the value for the first of the multiple observations are different from the set of parameters used to assign the value for the second of the multiple observations.

18. The method of claim 15, further comprising the step of: removing one or more of the multiple observations that are determined to have inadequate data quality.

19. The method of claim 18, further comprising the step of: recording additional observations based how many of the one or more multiple observations were removed.

20. The method of claim 15, wherein one or more of the M observations are of the same individual polymer.

21. The method of claim 13, further comprising the step of: systematically altering the first iteration sequence to maximize a combined probability of the first iteration sequence leading to the M observations in order to obtain a most likely sequence of monomers of the polymer.

22. The method of claim 13, wherein assigning the value to each pore blocking signal includes:
estimating a number of repeat instances of each monomer in the observation to obtain an estimated number of repeat monomers; and
applying a $4^n$-state Hidden Markov Model to the observation to obtain the trial sequence, wherein n is the estimated number of monomers contributing to the measured signal.

23. The method of claim 22, wherein the $4^n$-state Hidden Markov Model is a four-state Hidden Markov Model.

24. The method of claim 13, wherein the step of calculating the probabilities includes applying a Sequence Hidden Markov Model to each of the M trial sequences, wherein a transition probability parameter of the Sequence Hidden Markov Model depends on a direction of a previous monomer hop during sequencing.

25. The method of claim 13, further comprising:
running each of the M sequence Hidden Markov Models through a forward-Viterbi algorithm to obtain the first iteration sequence.

26. The method of claim 13, wherein the polymer is DNA.

27. The method of claim 13, wherein the series of distinct pore blocking signals are obtained using a protein pore current blockage process.

28. The method of claim 13, wherein the portion of the polymer constitutes the entire polymer.

* * * * *

SEQUENCE LISTING

<160> NUMBER OF SEQ ID NOS: 115

<210> SEQ ID NO 1
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 1
tcggactagc ccttagcaat cgaaa                                          25

<210> SEQ ID NO 2
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 2
tcgactagcc cttagcaatc gaaa                                           24

<210> SEQ ID NO 3
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 3
gtactgggcc cactagctag cacgt                                          25

<210> SEQ ID NO 4
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 4
gtactgggcc cactagctag cacgt                                          25

<210> SEQ ID NO 5
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 5
tcggcttacc attctagaga tgcac                                          25

<210> SEQ ID NO 6
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 6
tcggacttac cattctagag atgcac                                         26

<210> SEQ ID NO 7
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 7
agtaccttcc ggccctccga ccact                                          25

<210> SEQ ID NO 8
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 8
agtaccttcc ggcccctcga cccact                                         26

<210> SEQ ID NO 9
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 9
attcaatcct caatattgca cctac                                          25

<210> SEQ ID NO 10
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 10
atcaatcctc aaattatgca cctac                                          25

<210> SEQ ID NO 11
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 11

```
ttcacaacag ctgccatacg ccggg                                          25

<210> SEQ ID NO 12
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 12
ttcacaacag ctgccatacg ccggg                                          25

<210> SEQ ID NO 13
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 13
ggggattaac atcctgcact caagc                                          25

<210> SEQ ID NO 14
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 14
gggataacat cctgccactc aagc                                           24

<210> SEQ ID NO 15
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 15
agaattggtt ctcgatagct ctata                                          25

<210> SEQ ID NO 16
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 16
agaatggttt ctcgatagct ctatta                                         26

<210> SEQ ID NO 17
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 17
atagcgatct cgggaagcaa gttgt                                          25
```

<210> SEQ ID NO 18
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 18
atagcgatct cggaagcaag tgtt                                          24

<210> SEQ ID NO 19
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 19
ttccaaggaa ccggtcggta gcaga                                         25

<210> SEQ ID NO 20
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 20
ttccaaggaa ccggtcggta gcaga                                         25

<210> SEQ ID NO 21
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 21
gactcgagct tcggacgtca aacat                                         25

<210> SEQ ID NO 22
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 22
gactcgagct tcgacgtcaa acat                                          24

<210> SEQ ID NO 23
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 23
atgggtatat cctcccgttc tgagt                                         25

```
<210> SEQ ID NO 24
<211> LENGTH: 25
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (9)..(10)
<223> OTHER INFORMATION: n is a, c, g, or t

<400> SEQUENCE: 24
atgggtatnn cctcccgttc tgagt                                            25

<210> SEQ ID NO 25
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 25
gcctgggtaa ggaaagcatc tcggc                                            25

<210> SEQ ID NO 26
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 26
gcctgggtaa aggaaagcat ctcgc                                            25

<210> SEQ ID NO 27
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 27
ggaatccaac attctatcgc tggaa                                            25

<210> SEQ ID NO 28
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 28
ggatccaaac attctatcgc tgaa                                             24

<210> SEQ ID NO 29
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 29
ctaaccacag acatctgcgg gaa                                              23
```

-continued

```
<210> SEQ ID NO 30
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 30
ctaaaacacc agacatctgc gggaa                                           25

<210> SEQ ID NO 31
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 31
tgttttgtct ggcctagcct acgga                                           25

<210> SEQ ID NO 32
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 32
tgttttgtct ggcctagcct acgga                                           25

<210> SEQ ID NO 33
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 33
cgaaatcata aggaagtcgg accgc                                           25

<210> SEQ ID NO 34
<211> LENGTH: 27
<212> TYPE: DNA
<213> ORGANISM: Artificial Sequence
<220> FEATURE:
<223> OTHER INFORMATION: This sequence was randomly generated by a
      computer

<400> SEQUENCE: 34
cgaaatcatt aaggaagtcg gaccgc                                          27

<210> SEQ ID NO 35
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 35
tcccctactt tagtaaaaca atcac                                           25
```

```
<210> SEQ ID NO 36
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 36
tcccctactt tagtaaaaca tcac                                          24

<210> SEQ ID NO 37
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 37
tttgatacaa taacgcgcta gttcc                                         25

<210> SEQ ID NO 38
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 38
tttgataaca taacgcgcta gttcc                                         25

<210> SEQ ID NO 39
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 39
accatatagt ttattgcaat gtgat                                         25

<210> SEQ ID NO 40
<211> LENGTH: 26
<212> TYPE: DNA
<213> ORGANISM: Artificial Sequence
<220> FEATURE:
<223> OTHER INFORMATION: This sequence was randomly generated by a
      computer

<400> SEQUENCE: 40
acattatagt ttatgcaatg ttgaat                                        26

<210> SEQ ID NO 41
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 41
tgcccttcaa tgcactgtgt catgg                                         25

<210> SEQ ID NO 42
<211> LENGTH: 25
```

```
<212> TYPE: DNA
<213> ORGANISM: Artificial Sequence
<220> FEATURE:
<223> OTHER INFORMATION: This sequence was randomly generated by a
      computer

<400> SEQUENCE: 42
tgccttcaat gcactgttgt catgg                                              25

<210> SEQ ID NO 43
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 43
ttgccgtccc tataatcatg tgcat                                              25

<210> SEQ ID NO 44
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 44
ttgccgtcct ataatcatgt gcat                                               24

<210> SEQ ID NO 45
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 45
taacctagtg aacgtacttc gagcc                                              25

<210> SEQ ID NO 46
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 46
tactagtgaa cgtacttcga gcc                                                23

<210> SEQ ID NO 47
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 47
gttgacatac aaggttttac tcttg                                              25

<210> SEQ ID NO 48
<211> LENGTH: 24
<212> TYPE: DNA
<213> ORGANISM: Artificial Sequence
```

<220> FEATURE:
<223> OTHER INFORMATION: This sequence was randomly generated by a
      computer

<400> SEQUENCE: 48
gtgacataca aggttttact cttg                                          24

<210> SEQ ID NO 49
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 49
ctccgtgcga tattagttgc aaatg                                         25

<210> SEQ ID NO 50
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 50
ctcgtgcgat attagttgca aatg                                          24

<210> SEQ ID NO 51
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 51
gtagccatta gttcgctgac tcccc                                         25

<210> SEQ ID NO 52
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 52
gtagccatta gttcgctgac tcccc                                         25

<210> SEQ ID NO 53
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 53
ggtccgtagt atgtacttca ctgaa                                         25

<210> SEQ ID NO 54
<211> LENGTH: 25
<212> TYPE: DNA
<213> ORGANISM: Artificial Sequence
<220> FEATURE:
<223> OTHER INFORMATION: This sequence was randomly generated by a -continued

```
      computer

<400> SEQUENCE: 54
ggtccgtagt atgtacttca ctgaa                                            25

<210> SEQ ID NO 55
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 55
tacaaatcgg actggagagt gtggg                                            25

<210> SEQ ID NO 56
<211> LENGTH: 27
<212> TYPE: DNA
<213> ORGANISM: Artificial Sequence
<220> FEATURE:
<223> OTHER INFORMATION: This sequence was randomly generated by a
      computer

<400> SEQUENCE: 56
tacaaatcgg actgggagag ttgtggg                                          27

<210> SEQ ID NO 57
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 57
agtgcattag atgcgcaccg ccgat                                            25

<210> SEQ ID NO 58
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 58
agtgcattag atgcgcacgc ccgat                                            25

<210> SEQ ID NO 59
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 59
aatcgcgggg taccaaccat ctaag                                            25

<210> SEQ ID NO 60
<211> LENGTH: 24
<212> TYPE: DNA
<213> ORGANISM: Artificial Sequence
<220> FEATURE:
<223> OTHER INFORMATION: This sequence was randomly generated by a
      computer
```

```
<400> SEQUENCE: 60
aatcgcgggt accaaccatc taag                                             24

<210> SEQ ID NO 61
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 61
agttgcccat ccgcttgggc ttcgc                                            25

<210> SEQ ID NO 62
<211> LENGTH: 22
<212> TYPE: DNA
<213> ORGANISM: Artificial Sequence
<220> FEATURE:
<223> OTHER INFORMATION: This sequence was randomly generated by a
      computer

<400> SEQUENCE: 62
agttgcccat cgcttggctc gc                                               22

<210> SEQ ID NO 63
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 63
cgatatcggc tgaggcctaa cttca                                            25

<210> SEQ ID NO 64
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 64
cgatatcggc tgaggcctaa ctca                                             24

<210> SEQ ID NO 65
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 65
gggatcccta taagcgacga cgccc                                            25

<210> SEQ ID NO 66
<211> LENGTH: 24
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (10)..(12)
```

```
<223> OTHER INFORMATION: n is a, c, g, or t

<400> SEQUENCE: 66
gggatcctan nngcgacgac gccc                                              24

<210> SEQ ID NO 67
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 67
agagtggcac taaccaatac gtcga                                             25

<210> SEQ ID NO 68
<211> LENGTH: 25
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (3)..(4)
<223> OTHER INFORMATION: n is a, c, g, or t

<400> SEQUENCE: 68
agnntggcac taaccaatac gtcga                                             25

<210> SEQ ID NO 69
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 69
gtacgggtcg gcccgggcct cccta                                             25

<210> SEQ ID NO 70
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 70
gtacgggtcg gccgggcctc cta                                               23

<210> SEQ ID NO 71
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 71
tagagacggc tagaagtatg gagga                                             25

<210> SEQ ID NO 72
<211> LENGTH: 24
<212> TYPE: DNA
<213> ORGANISM: Artificial Sequence
```

```
<220> FEATURE:
<223> OTHER INFORMATION: This sequence was randomly generated by a
      computer
<220> FEATURE:
<221> NAME/KEY: misc_feature
<222> LOCATION: (4)..(5)
<223> OTHER INFORMATION: n is a, c, g, or t

<400> SEQUENCE: 72
tagnnacggc tagaagtatg agga                                              24

<210> SEQ ID NO 73
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 73
aacagatagg cttcagaata gtgga                                             25

<210> SEQ ID NO 74
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 74
aacagatagg cttcagatag tgga                                              24

<210> SEQ ID NO 75
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 75
ctcttaatga cgacctttaa gctgc                                             25

<210> SEQ ID NO 76
<211> LENGTH: 24
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (3)..(5)
<223> OTHER INFORMATION: n is a, c, g, or t

<400> SEQUENCE: 76
ctnnnaatga cgaccttaag ctgc                                              24

<210> SEQ ID NO 77
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 77
ggagccgtac gagagcccctt aagcg                                            25
```

<210> SEQ ID NO 78
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 78
ggagccgtac gagagccctt aagcg                                          25

<210> SEQ ID NO 79
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 79
ccataggcct agatccgtgt tccg                                           24

<210> SEQ ID NO 80
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 80
ccataggcct agatccgttg tccg                                           24

<210> SEQ ID NO 81
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 81
atccgcgaga atccgcagat gttta                                          25

<210> SEQ ID NO 82
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 82
atccgcgaga atccgcagat gttta                                          25

<210> SEQ ID NO 83
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 83
atcatatgct gctgcttttc ccgga                                          25

```
<210> SEQ ID NO 84
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 84
atcatatgct gctgcttttc ccgga                                              25

<210> SEQ ID NO 85
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 85
ccctagtcat cccacttcgt gtaaa                                              25

<210> SEQ ID NO 86
<211> LENGTH: 27
<212> TYPE: DNA
<213> ORGANISM: Artificial Sequence
<220> FEATURE:
<223> OTHER INFORMATION: This sequence was randomly generated by a
      computer

<400> SEQUENCE: 86
ccctagtcat cccactttcg ttgtaaa                                            27

<210> SEQ ID NO 87
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 87
gccgagatat tgaatgctaa tactg                                              25

<210> SEQ ID NO 88
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 88
gcgagatatt gaatgctaat actg                                               24

<210> SEQ ID NO 89
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 89
gttctcgtga tgggcttgca ctaca                                              25

<210> SEQ ID NO 90
<211> LENGTH: 23
```

```
<212> TYPE: DNA
<213> ORGANISM: Artificial Sequence
<220> FEATURE:
<223> OTHER INFORMATION: This sequence was randomly generated by a
      computer

<400> SEQUENCE: 90
gtctcgtgat ggcttgcact aca                                             23

<210> SEQ ID NO 91
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 91
gccatgcaac ctgtttcggg ttggc                                           25

<210> SEQ ID NO 92
<211> LENGTH: 23
<212> TYPE: DNA
<213> ORGANISM: Artificial Sequence
<220> FEATURE:
<223> OTHER INFORMATION: This sequence was randomly generated by a
      computer

<400> SEQUENCE: 92
gcatgcaacc tgtttcgggt tgc                                             23

<210> SEQ ID NO 93
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 93
actaagcacg gcgcgcgaca agag                                            24

<210> SEQ ID NO 94
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 94
actagcacgg cgctgcgaca agag                                            24

<210> SEQ ID NO 95
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 95
gccaaaccat cacatgccgc cctgg                                           25

<210> SEQ ID NO 96
<211> LENGTH: 23
<212> TYPE: DNA
<213> ORGANISM: Artificial Sequence
```

<220> FEATURE:
<223> OTHER INFORMATION: This sequence was randomly generated by a
      computer

<400> SEQUENCE: 96
gcaaccatca ccatgccgcc tgg                                       23

<210> SEQ ID NO 97
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 97
tccgcagcgc tcagggacga acttg                                     25

<210> SEQ ID NO 98
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 98
tccgcagcgc tcagggacga acttg                                     25

<210> SEQ ID NO 99
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 99
gtacaccatg ctccctgatg cccgt                                     25

<210> SEQ ID NO 100
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 100
gtacaaccat gctccctgat gccgt                                     25

<210> SEQ ID NO 101
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 101
acaaagcgac taaatgcctc cttca                                     25

<210> SEQ ID NO 102
<211> LENGTH: 25
<212> TYPE: DNA
<213> ORGANISM: Artificial Sequence
<220> FEATURE:
<223> OTHER INFORMATION: This sequence was randomly generated by a -continued

```
      computer

<400> SEQUENCE: 102
acaaagcgac taaatgcctc cttca                                             25

<210> SEQ ID NO 103
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 103
gagccgcgtg tataaagatt cccag                                             25

<210> SEQ ID NO 104
<211> LENGTH: 26
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (14)..(17)
<223> OTHER INFORMATION: n is a, c, g, or t

<400> SEQUENCE: 104
gagccgcgtg gtannnngat tcccag                                            26

<210> SEQ ID NO 105
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 105
caaccgtagt gtaccgaaaa ttcaa                                             25

<210> SEQ ID NO 106
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 106
caccgtagtg taccgaaaat tcaa                                              24

<210> SEQ ID NO 107
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 107
gtagtaatat atgtctttcc ggtct                                             25

<210> SEQ ID NO 108
<211> LENGTH: 25
<212> TYPE: DNA
<213> ORGANISM: Artificial Sequence
```

```
<220> FEATURE:
<223> OTHER INFORMATION: This sequence was randomly generated by a
      computer
<220> FEATURE:
<221> NAME/KEY: misc_feature
<222> LOCATION: (11)..(12)
<223> OTHER INFORMATION: n is a, c, g, or t

<400> SEQUENCE: 108
gtagtaatat nngtctttcc ggtct                                           25

<210> SEQ ID NO 109
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 109
cattacttac ggtacggatc actgg                                           25

<210> SEQ ID NO 110
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 110
catacttacg tacggatcac tggg                                            24

<210> SEQ ID NO 111
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 111
tcgtgtgcct tacgtaggga gttgt                                           25

<210> SEQ ID NO 112
<211> LENGTH: 25
<212> TYPE: DNA
<213> ORGANISM: Artificial Sequence
<220> FEATURE:
<223> OTHER INFORMATION: This sequence was randomly generated by a
      computer
<220> FEATURE:
<221> NAME/KEY: misc_feature
<222> LOCATION: (6)..(7)
<223> OTHER INFORMATION: n is a, c, g, or t

<400> SEQUENCE: 112
tcgtgnncct tacgtaggga gttgt                                           25

<210> SEQ ID NO 113
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 113
catggagtcg cgttacctag actga                                           25
```

```
<210> SEQ ID NO 114
<211> LENGTH: 24
<212> TYPE: DNA
<213> ORGANISM: Artificial Sequence
<220> FEATURE:
<223> OTHER INFORMATION: This sequence was randomly generated by a
      computer

<400> SEQUENCE: 114
catgagtcgc gttacctaga ctga                                              24

<210> SEQ ID NO 115
<211> LENGTH: 25
<212> TYPE: DNA
<213> ORGANISM: Artificial Sequence
<220> FEATURE:
<223> OTHER INFORMATION: This sequence was randomly generated by a
      computer

<400> SEQUENCE: 115
ccagttgaca aatggcccct gtaca                                             25
```